United States Patent [19]

Lev et al.

[11] Patent Number: 5,643,447

[45] Date of Patent: Jul. 1, 1997

[54] THIN LAYER CHROMATOGRAPHIC PLATES

[75] Inventors: Ovadia Lev; Michael Tsionsky, both of Jerusalem, Israel

[73] Assignee: Yissum Research Developement Company of the Hebrew University of Jerusalem, Jerusalem, Israel

[21] Appl. No.: 376,646

[22] Filed: Jan. 20, 1995

Related U.S. Application Data

[63] Continuation-in-part of Ser. No. 43,789, Apr. 6, 1993, abandoned.

[51] Int. Cl.⁶ .................................................. B01D 15/08
[52] U.S. Cl. ............................... 210/198.3; 210/658
[58] Field of Search ................................. 210/635, 656, 210/658, 198.2, 198.3

[56] References Cited

U.S. PATENT DOCUMENTS

| | | | |
|---|---|---|---|
| 4,010,242 | 3/1977 | Iler | 264/15 |
| 4,138,336 | 2/1979 | Mendel | 210/198.2 |
| 4,713,338 | 12/1987 | Oliver | 210/679 |
| 4,902,413 | 2/1990 | Stout | 210/198.2 |
| 4,902,426 | 2/1990 | Macedo | 210/656 |
| 4,904,291 | 2/1990 | Siebers | 65/18.1 |
| 4,971,697 | 11/1990 | Douden | 210/502.1 |
| 5,292,801 | 3/1994 | Avnir | 435/174 |

FOREIGN PATENT DOCUMENTS 0439318  7/1991  European Pat. Off. ........... 210/198.2

OTHER PUBLICATIONS

Stahl, E., "Thin-Layer Chromatography", Springer-Verlag, Berlin, 2nd Edition, (1969). pp. IX, 105, and 106.

Ulrich, D. R., "Prospects for Sol-Gel Processes", Journal of Non-Crystalline Solids, 121, pp. 465-479 (1990).

Jorgenson, J. W., "New Directions in Electrophoretic Methods", American Chemical Society, Symposium Series, vol. 335, Washington, D. C. (1987). pp. 1-19.

Brinker, C. J. et al., "The Physics and Chemistry of Sol-Gel Processing" Sol-Gel Science, Academic Press, (1990), pp. VII -X, 2,3,22,23, and 788.

Brinker, C. J. et al, "The Physics and Chemistry of Sol-Gel Processing", Sol-Gel Science, Academic Press, p. 787, (1990).

Philipp, G. et al, "New Materials for Contact Lenses Prepared from Si-and Ti-Alkoxides by the Sol-Gel Process", Journal of Non-Crystalline Solids 63, pp. 283-292 (1984).

Schmidt, H. et al., "Organically Modified Ceramics and their Applications", Journal of Non-Crystalline Solids 121, pp. 428-435 (1990).

Nakanishi, K. et al., "I. Gel Formation Behavior and Effect of Solvent Composition", Journal of Non-Crystalline Solids 139 pp. 1-13 (1992).

Stahl, E., "Thin-Layer Chromatography", Springer-Verlag, Berlin, pp. 889 (1969).

Primary Examiner—Ernest G. Therkorn
Attorney, Agent, or Firm—Foley & Lardner

[57] ABSTRACT

The invention provides a planar chromatographic plate comprising a supported homogeneous thin porous film of ceramic material produced by sol-gel technology the film being provided with a porous network enabling elution through the film whereby planar chromatographic separation of chemicals or biochemicals can be carried out therewith.

11 Claims, 2 Drawing Sheets

THIN LAYER CHROMATOGRAPHIC PLATES

This application is a continuation-in-part, of application Ser. No. 08/043,789, filed Apr. 6, 1993, now abandoned.

The present invention relates to thin layer planar chromatographic plates and to methods for the preparation thereof. More particularly the present invention relates to planar thin layer chromatographic plates comprising a supported homogeneous thin porous film of ceramic material produced by sol-gel technology.

Planar chromatographic methods such as thin layer chromatography, paper chromatography, and field assisted techniques such as electrophoretic or gravity assisted planar chromatographies (see for example E. Stahl, Thin Layer Chromatography, 2nd ed., Springer-Verlag, Berlin (1969)) use thin layers of powdered porous silica, alumina or other powders attached to the solid support by gypsum, starch, organic polymer or another binding material. For example, U.S. Pat. No. 4,138,336 describes a thin layer chromatographic plate which includes a substrate having a layer of discrete spherical inorganic metal oxide ceramic chromatographic particles bonded thereto with an inorganic metal oxide binder.

In contradistinction thereto, the present invention relates to a method to produce and use a new type of chromatographic plate using homogeneous thin silica (or other metal oxide) films prepared by the sol-gel process, instead of conventional layers of powdered oxides. In other words, the homogenous thin films of the present invention do not require either powdered porous silica or binders and, therefore, can be made substantially free therefrom.

Thin films of silica and other oxides have found many applications as protective coatings, solar energy convertors, catalysts and other photometric devices (D. H. Ulrich, Prospects of the sol-gel processes Journal of Non-Crystalline Solids, 121, 465–479, 1990). However, despite the fact that sol-gel derived porous powders (e.g. silica gels) are commonly produced by sol-gel methods and are routinely used for chromatographic separations, there is no reported attempt to use sol-gel films in thin layer or any other planar chromatography material.

According to the present invention it has now been found that by using a modified sol-gel casting procedure it is possible to drive different solvents by capillarity forces through thin films of silica produced by the sol-gel process. This opened the door for the application of thin sol-gel films for chromatographic separation purposes. For example, the present inventors have been able to demonstrate the separation and quantification of several amino-acids and some common dyes by the newly invented thin film chromatography (TFC).

The present invention relates to a new type of separating media for planar chromatography and also to the method of producing such chromatographic media.

Planar chromatographic methods: Planar chromatography is a diverse scientific technology, which ranges from the very cheap thin layer chromatographic media to sophisticated and powerful electrophoretic chromatographies and from the qualitative identification methods to powerful quantitative densitometric techniques.

Planar chromatographic separations include thin layer chromatography and the related planar chromatographic processes wherein an external force such as gravitation, evaporation or centrifugation is used to drive the eluent through the chromatographic media and include planar electrophoretic techniques such as those mentioned in J. W. Jorgenson, Overview of Electrophoresis, in New Directions in Electrophoretic methods, ACS. Symp. Series Vol. 335, J. W. Jorgenson and M. Phillips, eds, Am. Chem. Soc. Washington, D.C. 1987.

Despite its powerful capabilities the majority of thin layer chromatographic devices still rely on relatively simple powdered silica gel and alumina separating media.

The progress in the production of chromatographic media for high performance liquid chromatography (HPLC) and gas chromatography (GC) was not matched by such a progress in (the application of) thin layer chromatographic technology, probably due to the fact that thin layer chromatographic plates are disposable and therefore there is little incentive in devoting expenditures to the production of tailored, specific and therefore more expensive media.

Sol-gel technology: Sol-gel technology is a general name for the production of silica and metal oxide ceramics by meltless processes through the polymerization of suitable monomers (such as the metal alkoxides), which produce colloidal suspension (sol) and upon further agglomeration produce the xerogel ("dry gel") state.

Sol-gel glass is any ceramic or organoceramic material as depicted generally in C. J. Brinker and G. W. Scherer, "Sol-Gel Science", Academic Press, San-Diego, (1990) the teachings of which are incorporated herein by reference.

Hydrolysis and condensation: Most of the sol-gel techniques use low molecular weight tetraalkoxysilane precursors, such as tetramethoxysilane (TMOS) or tetraethoxysilane (TEOS), although it is also possible to use sodium silicate precursors. The overall chemical reaction is given by:

$$Si(OR)_4 + (4-x)H_2O \longrightarrow SiO_x(OH)_{4-2x} + 4ROH \qquad (1)$$

The reaction proceeds through hydrolysis (EQ. 2) and condensation (EQ. 3) steps:

$$\equiv Si-OR + H_2O \longrightarrow \equiv Si-OH + ROH \qquad (2)$$

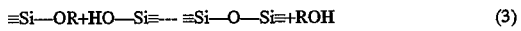
$$\equiv Si-OR + HO-Si \equiv \longrightarrow \equiv Si-O-Si \equiv + ROH \qquad (3)$$

Since alkoxsilane is not miscible in aqueous solution methanol or another solvent, e.g. THF (Tetrahydrofuran) or an alcohol, is used for homogenization.

Gelation: Unlike organic polymerization that is governed by the formation of chain polymers, which branch and crosslink to form the gel, silica "polymerization" is believed to evolve through the formation of a colloidal suspension (the "sol") which gels by agglomeration. Since silica oligomers are silanol rich, the pH level strongly influences the kinetics of the agglomeration and the final structure of the xerogel. High pH conditions produce condensed particulate sols, which eventually agglomerate to give highly porous silica gels. Low pH (2–7) polymerization gives branched polymeric sols and dense, high surface area (up to ca 1000 $m^3/gr$) gels.

Drying: During the last stage of the gelation, water and solvent evaporate from the glass cavities forming the dry gel (xerogel) state.

Sintering: A high temperature sintering step is used to densify the porous layer and to form poreless films or monoliths. This step is omitted or used mildly in the preparation of the thin film chromatographic media since the porous structure is essential for eluent penetration and the chromatographic separation.

Using adequate procedures, it is possible to produce ceramics in various configurations, such as thin films, powders, fibers and monoliths, from various metal oxides such as titania, silica, alumina and vanadium oxides and mixed oxides of different compositions. (J. Brinker and G. W. Scherer, Sol-Gel Science, Academic Press, 1990, pp. 787).

By using a different type of precursors it is possible to produce modified silica matrices with controlled surface properties. For example, a mixture of methyltrimethoxysilane (MTMOS) and tetramethoxysilane (TMOS) monomers gives:

$(2-x)\ Si(OCH_3)_4 + (x-y)\ (CH_3)Si(OCH_3)_3 + (2-x+y)\ H_2O \longrightarrow$
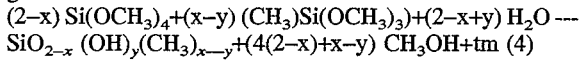
$SiO_{2-x}\ (OH)_y(CH_3)_{x-y} + (4(2-x)+x-y)\ CH_3OH + tm$ (4)

Replacing the methyl group in the methyltrimethoxy with octadecyl or another radical (such as phenyl, aminoalkyl or cyanoalkyl) will affect the surface properties of the material (G. Philipp and H. Schmidt, J. of Non-Crystalline Solids 63, 283 (1984); H. Schmidt, J. of Non-Crystalline Solids 121 428 (1990)).

According to the present invention it has now been found that by incorporation of large concentrations of suitable pore-forming organic compounds such as, e.g. polymers or dyes along with the polymerization precursors and leaching of these compounds after the film is dried it is possible to produce thin silica films with large pores (0.1–10 μm) that intercalate within the thin film and so facilitate an upward migration of the eluent through the porous capillary-like structure.

Thus according to the present invention there is now provided a planar chromatographic plate comprising a supported homogeneous thin porous film of ceramic material produced by sol-gel technology, said film being provided with a porous network enabling elution through the film whereby planar chromatographic separation of chemicals or biochemicals can be carried out therewith.

In preferred embodiments of the present invention said pores are in the range of about 0.05 to about 10 μm.

Preferably said ceramic film is silica, titania, alumina or a mixture thereof.

The invention also provides a method for the preparation of a thin layer planar chromatographic plate as hereinbefore defined comprising coating a solid support with a solution containing the precursors of the sol-gel process and a pore-forming organic compound and subsequently leaching said compound from the ceramic or organoceramic film after gel formation.

A related technique for the control of pore size distribution by addition of water soluble polymers to the sol-gel polymerization precursors (but without its subsequent leaching), was developed by K. Nakanishi and N. Soga, J. Non Crystaleine Solids, 139, 1 (1992)). However these authors use their technique for the production of monolithic xerogels and not for thin films and did not suggest the use thereof for molding of thin film chromatographic media.

It is further important to note that a porous structure with pores that are perpendicular to the supporting matrix of the thin film will not facilitate capillarity suction, eluent migration and chromatographic separations. However, the films of the present invention are provided with a porous intercalated network having a plurality of intercalated pores, which enables eluent migration and chromatographic separations in a direction substantially parallel to the supporting substrate. Thus, for the first time the present invention teaches the formation of homogenous, porous thin films with intercalated open channels that enable elution of a solvent through the film and parallel to the supporting substrate.

In European Patent application publication no. 439318 there is taught and claimed a method for obtaining an interaction between reagent/s in a solid support and diffusible solute/s or components in an adjacent liquid or gas phase wherein said reagent/s are trapped in a sol-gel glass (hereinafter also referred to as doped sol gel glass) which provides the solid support to the reagents, wherein a sol-gel glass is any ceramic or organoceramic material prepared by polymerization of suitable monomers, such as metal alkoxide mixtures, wherein the polymerization is carried out through the sol gel-xerogel stages.

As will be realised however said description is limited to doped sol-gel glasses which are not homogeneous and does not teach or suggest how to prepare a thin porous film for use in planar chromatographic separations since normal thin films do not possess pores which will enable elution. In other words, the homogeneous films of the present invention do not include or retain "dopants" such as those described in U.S. Pat. No. 5,292,801 or European Patent Application No. 439 318.

The proposed methods offers the following advantages:
a) Control over the physical characteristics of the thin film including its thickness (and thus radiation scattering and optical pathlength);
b) controlled pore size distribution which affects the light scattering and the rate of eluent flowrate;
c) production of homogeneous films. The homogeneity of the thin sol-gel films affects its metrological characteristics and detection range;
d) very good adhesion of these films to supporting matrices;
e) inherent transparency (both in UV and visible range) of silica derived thin films; and
f) versatility of the sol-gel manufacturing technology, i.e., the ability to tailor surfaces with any desired polarity, ion exchange capacity or chemical affinity.

The invention will now be described in connection with certain preferred embodiments in the following examples and with reference to the following illustrative figures so that it may be more fully understood.

The following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention. While the invention will now be described in connection with certain preferred embodiments in the following examples and with reference to the accompanying figures so that aspects thereof may be more fully understood and appreciated, it is not intended to limit the invention to these particular embodiments. On the contrary, it is intended to cover all alternatives, modifications and equivalents as may be included within the scope of the invention as defined by the appended claims.

A. the upper layer of the TFC plate;

B. cross section of the porous structure of the chromatographic media; and

C. cross section of the supporting glass slide.

Figure 3:
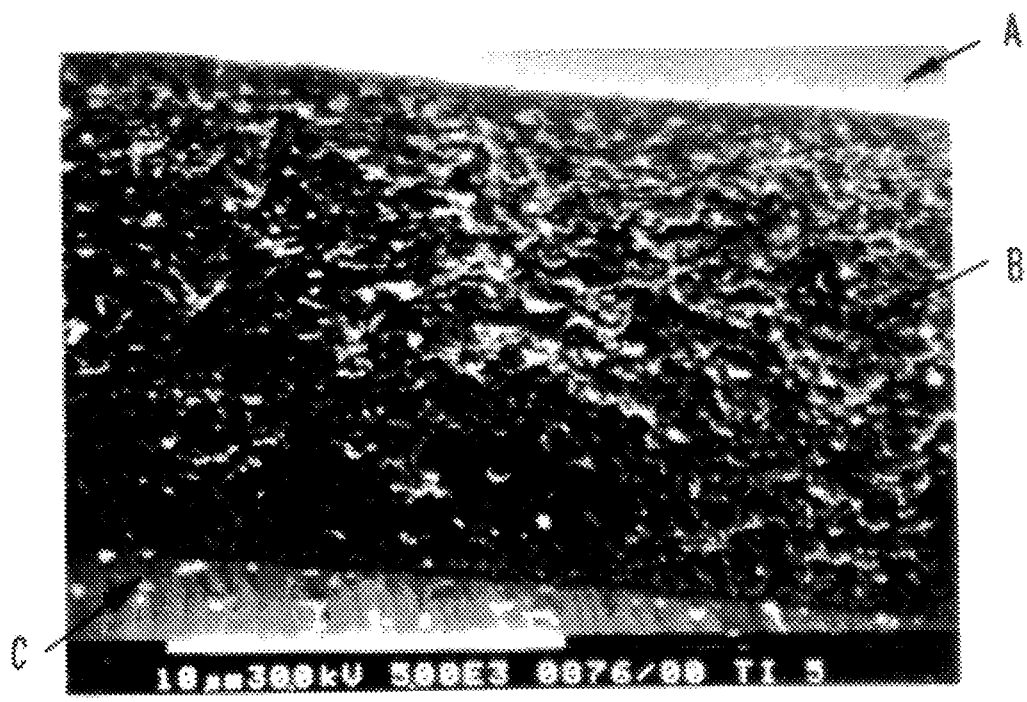

FIG. 3 depicts SEM micrograph of a tilted mixed titania-silica TFC plate (prepared according to the protocol of example 2): showing:

A. the upper layer of the TFC plate,

B. cross section of the porous structure of the chromatographic media, and

C. cross section of the supporting glass slide.

DESCRIPTION OF THE PREFERRED
EMBODIMENTS

EXAMPLES

Example 1

Solvent Migration

Preparation of the xerogel film: 1.5 ml methanol (Fluka), 0.5 ml methyltrimethoxysilane (MTMOS), 0.05 ml hydrochloric acid (11M), 0.01 ml of 50% aqueous solution of n-[(3trimethoxysilyl)-propyl]ethylenediamine tri-acetic acid tri-sodium salt, and 0.18 gr. bromocresol purple were mixed for 4 minutes under vigorous agitation. 25×75 mm microscope slides were coated with 0.2 ml of fresh solution and dried overnight in ambient conditions. This preparation resulted in 10–12 μm uniform film, except near the boundary of the glass slide, where the film became thicker (but this part of the thin layer can be scratched away). After rinsing of the plates with ethanol and leaching of the dopant a white opaque thin xerogel film coating is produced.

Eluent migration in the thin film chromatography (TFC) was conducted by placing the TLC plate in a glass saturation chamber approximately 5 mm above the solvent level and attaching a saturation paper pad (Alltech) to connect between the bottom of the TLC plate and the solvent (i.e. the eluent).

Example 2

Separation of Amino Acid Mixture

Study of the separation of several amino acids was conducted using the TFC plates described in example 1. 1:1 methanol:ethanol eluent was used. Spot visualization was conducted when the eluent front reached 4.4 cm from the center of the application point. Visualization was conducted by spraying the TFC plate with 1.0% ninhydrin alcohol solution containing 3% acetic acid solution (E. Stahl, Thin Layer Chromatography, 2nd ed., Springer-Verlag, Berlin (1969), pp. 889).

HRf % value of some amino-acids are depicted in Table 1.

TABLE 1

HRf % values of amino-acid separation by thin film chromatography (TFC) and conventional TLC (Merck).

| | | Eluent | | |
| --- | --- | --- | --- | --- |
| | | Methanol/Ethanol | | Water/Ethanol |
| Amino-acid | Amount | TFC | TLC | TLC |
| Tryptophane | 0.1 μg | 83 | 48 | 65 |
| DL-Alanine | 0.01 μg | 79 | 18 | 47 |
| L-Proline | 0.1 μg | 62 | 22 | 35 |
| L-Histidine | 0.3 μg | 29 | 6 | 33 |
| Arginine | 0.1 μg | 3 | 0 | 4 |

HRf = 100 × [(the migration distance of the center of the spot)/(distance of front propagation)]

TABLE 2

HRf % values for separation of dyes by TFC and conventional TLC plates.

| Dye | HRf % | HRf %* |
| --- | --- | --- |
| Methyl Red | 75 | 55 |
| Bromocresol Green | 50 | 22 |
| Thimol Blue | 10 | 67 |

*data obtained in conventional TLC plates using solvent Toluene:Methanol (6:1)

Example 3

Separation of Dyes

Study of the migration of several dyes was conduction using TFC plates produced by the following procedure: 1.5 ml methanol (Fluka), 0.5 ml methyltrimethoxysilane (MTMOS), 0.05 ml hydrochloric acid (11M) and 0.18 gr. bromocresol purple were mixed for 4 minutes under vigorous agitation. 25×75 mm microscope slides were coated with 0.2 ml of fresh solution and dried overnight in ambient conditions. 6:1 Toluene:methanol eluent was used. Spot visualization was conducted when the eluent front reached 4.4 cm from the center of the application point. HRf% values are listed in Table 2.

Example 4

Structural Studies

Figure 2:
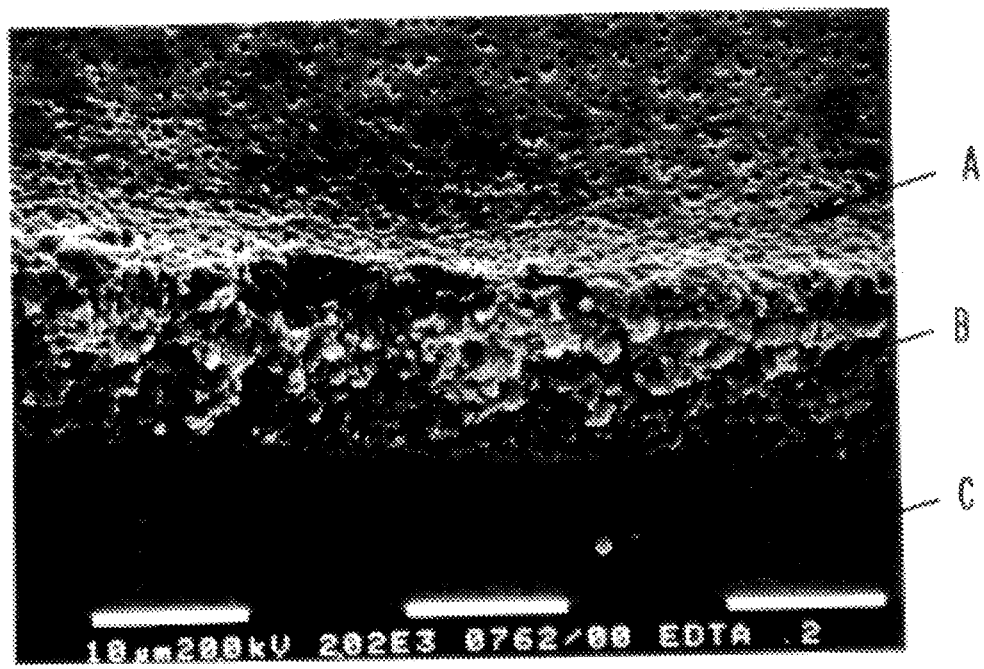
FIG. 2 depicts SEM micrograph of a tilted TFC plate showing (prepared according to the protocol of example 1 and the following are the appropriate captions thereof.

FIG. 2 depicts scanning electron microscopy (SEM) micrograph of modified silica sol-gel plate according to the protocol of example 1. The thin film chromatographic plate was tilted so that the upper section of the micrograph (marked A) depicts the upper surface of the chromatographic media, region B depicts a cross section of the TFC media and C marks the supporting glass plate. It is interesting to note that a SEM micrograph taken from above will give a misleading notion of the true characteristics of the porous structure of the thin film.

Example 5

Mixed Metal Oxides

Figure 1:
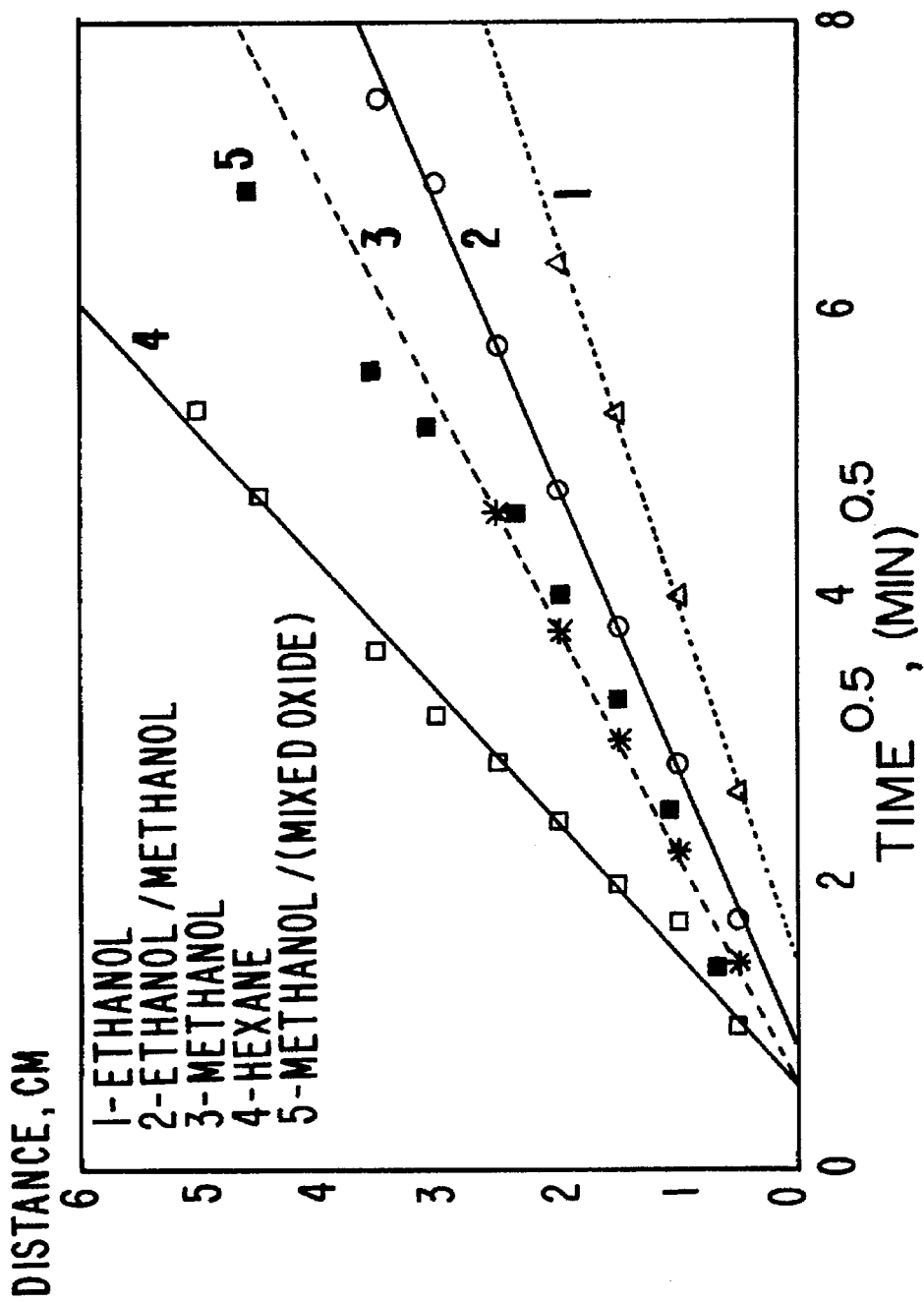
FIG. 1 which should be read in conjunction with Example 1 depicts the level of the propagating wet front versus elution time for several eluents (1:1 methanol:ethanol solution, ethanol, methanol and hexane). The observed induction time is the time required for the saturation of the paper pad. Said figure shows propagation distance of wet front versus $t^{0.5}$ (t=elution time in minutes) for different solvents eluting in a TFC plate prepared according to the protocol of example 1 (curves 1–4) and example 5 (curve 5).

One of the advantages of the sol-gel process is to produce mixed ceramics. FIG. 3 depicts scanning electron microscopy (SEM) micrograph of titania—silica sol-gel plate that was prepared according to the following protocol: 1.5 ml methanol (Fluka), 0.5 ml methyltrimethoxysilane (MTMOS), 0.05 ml hydrochloric acid (11M), 0.01–0.04 ml of titanium (IV) propoxide 98% (Aldrich) and 0.18 gr. bromocresol purple were mixed for 4 minutes under vigorous agitation. 25×75 mm microscope slides were coated with 0.2 ml of fresh solution and dried overnight in ambient conditions. This preparation resulted in 10–12 μm uniform film. The thin film chromatographic plate was tilted so that the upper section of the micrograph (marked A) depicts the upper surface of the chromatographic media, region B depicts a cross section of the TFC media and C marks the supporting glass plate. The rate of elution of methanol through this chromatographic media is depicted by full square symbols in FIG. 1 (curve 5).

Example 6

Adhesion Studies

The adhesion of the chromatographic media in TFC and conventional commercial TFC (Merck cat no. 5724) plates were compared using Instron M1114 Universal Testing Machine. Breakpoint shear force was ca. 2–3 Kg/cm$^2$ for TFC plates and the TFC plate withstood 60 Kg/cm$^2$ shear force (at that point support failure prevented additional tension loading).

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A planar chromatographic plate comprising a supported homogeneous thin porous film of ceramic material produced by sol gel technology, said film being provided with a porous intercalated network, having a plurality of intercalated pores, enabling capillary suction, eluent migration and chromatographic separation through the film pores, in a direction substantially parallel to the supporting substrate, whereby planar chromatographic separation of chemicals or biochemicals can be carried out therewith.

2. A planar chromatographic plate according to claim 1 wherein said pores are in the range of about 0.05 to about 10 μm.

3. A planar chromatographic plate according to claim 1 wherein said ceramic film is silica, titania, alumina or a mixture thereof.

4. A planar chromatographic plate according to claim 1, said plate being prepared by a process comprising the steps of:

coating a solid support with a solution containing the precursors of a sol-gel process and a pore-forming organic compound;

polymerizing said precursors to form a solid xerogel film of ceramic material; and subsequently leaching said compound from the ceramic or organoceramic film after gel formation;

whereby there is formed a supported thin porous film provided with a porous intercalated network having a plurality of intercalated pores, enabling capillary suction, eluent migration and chromatographic separation therethrough, in a direction substantially parallel to the supporting substrate.

5. A planar chromatographic plate according to claim 4, wherein said pore-forming compound comprises a polymer.

6. A planar chromatographic plate according to claim 4, wherein said pore-forming compound comprises a dye.

7. A planar chromatographic plate according to claim 4, wherein said pores are in the range of about 0.1 to 10 microns.

8. A planar chromatographic plate according to claim 1, wherein said ceramic material is a titania-silica mixture.

9. A planar chromatographic plate according to claim 1, wherein said homogeneous thin porous film contains no binders.

10. A planar chromatographic plate according to claim 1, wherein said homogeneous thin porous film is a xerogel.

11. A planar chromatographic plate which comprises a supporting substrate and a homogeneous thin porous film, wherein said film consists essentially of a homogenous xerogel film having a plurality of intercalated pores therein, enabling capillary suction, eluent migration and chromatographic separation in a direction substantially parallel to the supporting substrate.

* * * * *